United States Patent
Cohen-Solal et al.

(10) Patent No.: US 10,600,136 B2
(45) Date of Patent: Mar. 24, 2020

(54) IDENTIFICATION OF MEDICAL CONCEPTS FOR IMAGING PROTOCOL SELECTION

(75) Inventors: Eric Cohen-Solal, Ossining, NY (US); Michael Chun-Chieh Lee, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1037 days.

(21) Appl. No.: 13/981,998

(22) PCT Filed: Jan. 31, 2012

(86) PCT No.: PCT/IB2012/050435
§ 371 (c)(1),
(2), (4) Date: Jul. 26, 2013

(87) PCT Pub. No.: WO2012/104780
PCT Pub. Date: Aug. 9, 2012

(65) Prior Publication Data
US 2013/0311200 A1    Nov. 21, 2013

Related U.S. Application Data

(60) Provisional application No. 61/439,484, filed on Feb. 4, 2011.

(51) Int. Cl.
*G06Q 50/22* (2018.01)
*G06F 19/00* (2018.01)
(Continued)

(52) U.S. Cl.
CPC .......... *G06Q 50/22* (2013.01); *G06F 19/321* (2013.01); *G06Q 10/06* (2013.01); *G16H 50/70* (2018.01)

(58) Field of Classification Search
CPC ....... G06C 50/22; G06C 50/24; G06F 19/322; G06F 19/323–327; G06Q 50/22; G06Q 50/24
(Continued)

(56) References Cited

U.S. PATENT DOCUMENTS 6,287,257 B1 *  9/2001  Matichuk ................. A61B 8/00
                                                        600/437
7,244,230 B2    7/2007  Duggirala et al.
(Continued)

FOREIGN PATENT DOCUMENTS

DE  102008002882 A1  1/2009
WO  2000007131 A1    2/2000
WO  2002033654 A1    4/2002

OTHER PUBLICATIONS

Chandoo.org, Even Faster Way to Compare 2 Lists in Excel, Jul. 1, 2010, 17 pages.*
(Continued)

*Primary Examiner* — Jason S Tiedeman (57) ABSTRACT

A method includes identifying medical concepts in identified patient cases that are missing from medical concepts in first electronically formatted medical information as missing medical concepts, and selecting an imaging protocol for an imaging procedure based on a combination of the medical concepts from the first electronically formatted medical information and the missing medical concepts, and generating a signal indicative of the selected imaging protocol. A method includes identifying at least one of one or more medical concepts as a relevant additional concept, and selecting an imaging protocol for the imaging procedure based on a combination of one or more clinical indications and the relevant additional concept, and generating a signal indicative of the selected imaging protocol.

20 Claims, 6 Drawing Sheets

(51) Int. Cl.
*G06Q 10/06* (2012.01)
*G16H 50/70* (2018.01)

(58) Field of Classification Search
USPC .......................................................... 705/2, 3
See application file for complete search history.

(56) References Cited

U.S. PATENT DOCUMENTS

| | | | |
|---|---|---|---|
| 2002/0129031 A1 | 9/2002 | Lau et al. | |
| 2003/0069760 A1* | 4/2003 | Gelber | G06Q 40/02 705/4 |
| 2003/0092980 A1* | 5/2003 | Nitz | A61B 6/00 600/407 |
| 2003/0139944 A1* | 7/2003 | Carlsen | G06F 19/322 705/2 |
| 2003/0191666 A1* | 10/2003 | Kline | G06F 17/18 705/2 |
| 2004/0122709 A1* | 6/2004 | Avinash | G06F 19/322 705/2 |
| 2004/0147840 A1* | 7/2004 | Duggirala | A61B 8/00 600/437 |
| 2004/0175700 A1* | 9/2004 | Geesaman | C12Q 1/6883 435/6.11 |
| 2005/0010098 A1* | 1/2005 | Frigstad | A61B 5/0002 600/407 |
| 2005/0010445 A1* | 1/2005 | Krishnan | G06F 19/321 705/2 |
| 2005/0033121 A1* | 2/2005 | Modrovich | G06F 19/322 600/300 |
| 2005/0049497 A1 | 3/2005 | Krishnan et al. | |
| 2005/0121505 A1* | 6/2005 | Metz | G06Q 50/24 235/375 |
| 2005/0165285 A1* | 7/2005 | Iliff | A61B 5/0002 600/300 |
| 2005/0267348 A1* | 12/2005 | Wollenweber | A61B 6/032 600/407 |
| 2006/0059145 A1 | 3/2006 | Henschke et al. | |
| 2006/0100738 A1* | 5/2006 | Alsafadi | A61B 6/56 700/214 |
| 2006/0112050 A1* | 5/2006 | Miikkulainen | G06F 19/345 706/46 |
| 2007/0179814 A1 | 8/2007 | Hernandez et al. | |
| 2007/0238963 A1* | 10/2007 | Kaminaga | A61B 6/032 600/407 |
| 2008/0040150 A1* | 2/2008 | Kao | G06F 19/322 705/2 |
| 2008/0082361 A1* | 4/2008 | Marge | G06Q 50/22 705/2 |
| 2008/0114564 A1* | 5/2008 | Ihara | G06F 17/30321 702/158 |
| 2008/0119717 A1* | 5/2008 | Profio | G06F 19/327 600/407 |
| 2008/0133275 A1* | 6/2008 | Haug | G06Q 10/06 705/3 |
| 2008/0172249 A1* | 7/2008 | Glaser-Seidnitzer | G06Q 50/22 705/2 |
| 2009/0006131 A1* | 1/2009 | Unger | G06F 19/321 705/3 |
| 2009/0006132 A1* | 1/2009 | Avinash | G06Q 50/24 705/3 |
| 2009/0048866 A1* | 2/2009 | Mahesh | G06Q 50/22 705/2 |
| 2009/0228299 A1* | 9/2009 | Kangarloo | G06F 19/321 705/2 |
| 2010/0054555 A1* | 3/2010 | Owen | G06F 19/321 382/128 |
| 2010/0145723 A1 | 6/2010 | Hudson et al. | |
| 2010/0208959 A1* | 8/2010 | Ax | G06F 19/321 382/128 |
| 2010/0241472 A1* | 9/2010 | Hernandez | G06F 19/322 705/3 |
| 2010/0312798 A1* | 12/2010 | Dutta | G06F 19/3443 707/780 |
| 2011/0010192 A1* | 1/2011 | Backhaus | G06F 19/321 705/2 |
| 2011/0022622 A1* | 1/2011 | Boroczky | G06F 19/3443 707/769 |
| 2011/0046979 A1* | 2/2011 | Tulipano | G06F 19/325 705/2 |
| 2012/0008846 A1* | 1/2012 | Meetz | A61B 6/032 382/131 |
| 2012/0041277 A1* | 2/2012 | Ebadollahi | A61B 5/0205 600/301 |
| 2012/0041909 A1* | 2/2012 | Glaser-Seidnitzer | G01R 33/543 706/12 |
| 2012/0213326 A1* | 8/2012 | Walker | A61B 6/032 378/4 |
| 2012/0278105 A1* | 11/2012 | Luszcz | G06F 19/321 705/2 |
| 2012/0290324 A1* | 11/2012 | Ribbing | G06F 19/321 705/3 |
| 2013/0024213 A1* | 1/2013 | Poon | A61B 5/0002 705/3 |

OTHER PUBLICATIONS

Kahn, C. et al. "Phoenix an Expert System for Selecting Diagnostic Imaging Procedures". Investigative Radiology, 22(12): 978-80, Dec. 1987.

* cited by examiner

IDENTIFICATION OF MEDICAL CONCEPTS FOR IMAGING PROTOCOL SELECTION

FIELD OF THE INVENTION

The following generally relates to medical informatics and is described with particularly application to a system and/or method for identifying missing medical concepts for selecting an imaging protocol for an imaging procedure for a patient from medical concepts for imaging procedures for other patients and/or for identifying medical concepts from medical information for a patient in addition to an order prescribing an imaging procedure for the patient for selecting an imaging protocol for the imaging procedure.

BACKGROUND OF THE INVENTION

Radiology departments perform imaging procedures every day. Each of these procedures requires a set of precise specifications of their use called a protocol. An example of how a particular protocol is selected for a particular patient is described next in connection with typical workflow for a patient who is to be imaged via a computed tomography (CT), magnetic resonance imaging (MRI), positron emission tomography (PET), or other medical imaging scan.

A prescribed order from a referring physician for an imaging examination is received by a radiology department, imaging center or the like. The order typically describes the general type of examination (CT, MRI, PET, US, etc.) and the anatomy to be scanned. Additionally, the order will include the clinical indications that resulted in the order. The clinical indications usually include signs, symptoms, and clinical history, and may also include hypotheses of the underlying disease or condition or mention "rule-out," which also suggests potential conditions that should be investigated in particular.

A radiologist reviews the order and assigns an imaging protocol for the patient based on the specific clinical indications. This process is referred to herein as "protocoling". The imaging protocol defines the settings used on the imaging equipment to acquire the images, and directs the imaging technologist who operates the scanner in how to perform the examination. The selection of the protocol generally occurs before the patient is scanned, typically hours to days before the patient arrives for the examination.

By way of further example, a patient's imaging order may include the indication "hearing loss in left ear," with the note to perform an "MRI of the head." Within this general examination type, there are many options of clinical imaging protocols that are used specifically by the imaging centre or radiology department. Examples that are under the general category "MRI of the head" may include "brain tumor," "multiple sclerosis," "angiography," "MR without contrast," "internal auditory canal," "eye-orbit," to name a few. A radiologist reading this order may decide that the order is best fulfilled by using the "internal auditory canal" protocol.

The selection of the most adequate imaging protocol for a given patient is based upon the available information from the patient clinical record. The record includes the current imaging order from a referring physician, which contains the "clinical indications" that caused the patient to be referred to imaging. Unfortunately, in some instances, it is possible that missing pieces of information (such as other clinical indications) in the order could lead to a sub-optimal selection of the best imaging protocol. Furthermore, in some cases, clinical information, in addition to the information in the order, that would facilitate protocoling is absent from the patient record.

SUMMARY OF THE INVENTION

Aspects of the present application address the above-referenced matters, and others.

According to one aspect, a method includes obtaining first electronically formatted medical information about a patient scheduled for an imaging procedure via an imaging system, wherein the electronically formatted medical information includes medical concepts corresponding to the imaging procedure, obtaining second electronically formatted medical information with medical concepts for one or more imaging procedures for patients previously scanned, identifying patient cases corresponding to the second electronically formatted medical information that include one or more of the medical concepts of the first electronically formatted medical information, identifying medical concepts in the identified patient cases that are missing from the medical concepts in the first electronically formatted medical information as missing medical concepts, and selecting an imaging protocol for the imaging procedure based on a combination of the medical concepts from the first electronically formatted medical information and the missing medical concepts, and generating a signal indicative of the selected imaging protocol.

According to another aspect, a computing system includes computer readable storage medium encoded with instructions for determining one or more candidate relevant additional concepts and one or more processors configured to execute the instructions. The one or more processors, when executing the instructions, identify a medical concept utilized for selecting an imaging protocol for a previously scanned patient as a candidate missing medical concept in connection with patient information for a patient to be scanned, wherein the identified medical concept is absent from the patient information for the patient to be scanned and one or more medical concepts in the patient information for the patient to be scanned are included in the medical concepts for the previously scanned patient. A display is configured for presenting at least one candidate missing medical concept.

According to another aspect, a computing readable storage medium is encoded with computer readable instructions, which, when executed by one or more processors of a computing system, cause the computer system to identify and recommend at least one candidate missing medical concept in connection with identifying an imaging protocol for an imaging procedure for a patient, wherein the at least one candidate missing medical concept is a medical concept absent from patient medical information for the patient and present in patient medical information for previously scanned patients, wherein the patient medical information for the previously scanned patients includes at least one medical concept in common with the medical concepts from patient medial information for the patient.

According to one aspect, a method includes obtaining electronically formatted medical information about a patient scheduled for an imaging procedure via an imaging system, wherein the electronically formatted medical information includes a prescribed order corresponding to the imaging procedure and other information, extracting the prescribed order from the electronically formatted medical information, wherein the order at least includes one or more clinical indications for the imaging procedure and extracting the other information from the electronically formatted medical information, wherein the other information at least includes one or more medical concepts for the patient, identifying at least one of the one or more medical concepts as a relevant additional concept, and selecting an imaging protocol for the imaging procedure based on a combination of the one or more clinical indications and the relevant additional concept, and generating a signal indicative of the selected imaging protocol.

According to another aspect, a computing system including computer readable storage medium encoded with instructions for determining one or more candidate relevant additional concepts, and one or more processors configured to execute the instructions. The one or more processors, when executing the instructions, extract clinical indications from an order for an imaging procedure for a patient from electronically formatted medical information, extract one or more other medical concepts from the electronically formatted medical information for the patient, and identify at least one of the extracted one or more medical concepts as a candidate relevant additional concept used with the clinical indications for determining an imaging protocol for the imaging procedure. A display is configured for presenting at least one candidate relevant additional concept.

According to another aspect, a computing readable storage medium is encoded with computer readable instructions, which, when executed by one or more processor of a computing system, cause the computer system to identify and recommend at least one candidate relevant additional concept in connection with identifying an imaging protocol for an imaging procedure for a patient, wherein the at least one candidate relevant additional concept includes a medical concept that is absent from an order prescribing the imaging procedure and included in patient information for the patient.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
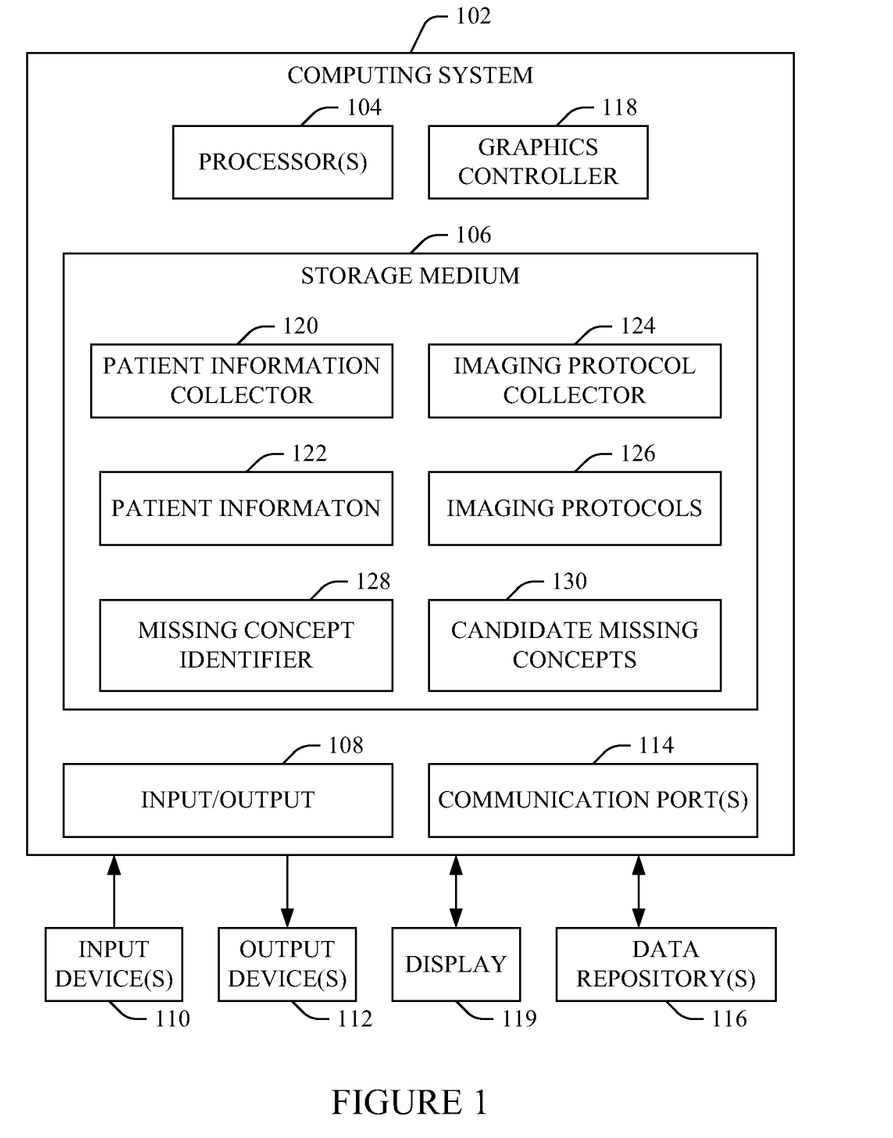
FIG. 1 illustrates an example system that includes a processor(s) and storage with computer readable instructions for identifying missing concepts for protocoling.

FIG. 1 illustrates an example computing system 102 such as a workstation, a computer, or the like. The computing system 102 includes one or more processors 104 and computer readable storage medium 106 (e.g., physical memory) encoded or embedded with computer readable instructions, which, when executed by the one or more processors 104 cause the system 102 to carry out various functions.

Although the storage medium 106 is showed as a single component, it is to be understood that the storage medium 106 may include a plurality of storage units, including storage local to the computing system 102 and/or storage external from the computing system 102. Additionally or alternatively, the one or more processors 104 execute instructions carried by transitory medium such as a signal carrier.

Input/output 108 is configured for receiving information from one or more input devices 110 (e.g., a keyboard, a mouse, and the like) and/or conveying information to one or more output devices 112 (e.g., a printer, a CD writer, a DVD writer, portable flash memory, etc.).

One or more communications ports 114 is configured for communication with an intranet (e.g., within a facility department), an internet (e.g., within and/or amongst facilities), and/or the Internet through various connectors, cables, interfaces, etc. In the illustrated embodiment, the one or more communications ports 114 are configured for communication with one or more data repositories 116.

In the context of imaging, the one or more data repositories 116 may include one or more of a picture archiving and communication system (PACS), a radiology information system (RIS), a hospital information system (HIS), an electronic medical record (EMR), a database, a server, an imaging system, a computer and/or other data repository. Such data may be stored in standard formats such as Digital Imaging and Communications in Medicine (DICOM), Health Level 7 (H17), and/or other standard formats, and/or non-standard, proprietary, and/or other format.

A graphics controller 118 processes data for presentation on a monitor such as display 119 in a human readable format.

The storage medium 106 stores various software applications and/or data, which are discussed next. As shown, in the illustrated embodiment, the storage medium 106 includes at least a patient information collector 120, collected patient information 122, an imaging protocol collector 124, collected imaging protocols 126, a missing concept identifier 128, and candidate missing concepts 130.

The patient information collector 120 communicates with various data repositories of the one or more data repositories 116 and/or other data repository(s) and retrieves electronically formatted information (patient information 122) therefrom for a particular subject scheduled to be scanned. With continuing reference to the radiology use case scenario, the patient information 122 at least includes clinical indications (e.g., signs, symptoms, etc.). Other information in the collected information includes, but is not limited to, physician prescribed order information, laboratory information, prior imaging reports, prior non-imaging reports, and/or other information.

The imaging protocol collector 124 also communicates with various data repositories of the one or more data repositories 116 and/or other data repository(s) and retrieves electronically formatted information therefrom. With continuing reference to imaging, the imaging protocol collector 124 at least collects existing imaging procedures or protocols 126.

The missing concept identifier 128 identifies candidate missing concepts 130 that are likely to facilitate protocoling and that are absent from the patient information 122. As described in greater detail below, in one instance, this is achieved by identifying patient cases, for patients previously scanned, that include the medical concepts from the patient information 122, and identifying one or more medical concepts in identified patient cases that are absent from the patient information 122 as the candidate missing concepts 130.

A candidate missing concept, in response to being confirmed as a relevant missing concept, may be displayed and used to facilitate mitigating sub-optimal protocoling due at least in part to protocoling without the missing medical concepts 130. Confirmation can be achieved through input provided by a radiologist or other authorized personnel, and may involve interaction with a referring physician, the patient, etc. to check if some of these terms apply to the patient situation. The missing concepts may lead to a more refined view of the patient condition and improved protocol selection.

In the illustrated embodiment, the patient information collector 120, the patient information 122, the imaging protocol collector 124, the imaging protocols 126, the missing concept identifier 128, and the candidate missing concepts 130 are shown in the storage medium 106. However, it is to be appreciated that one or more of 120-130 can be located in other local storage medium and/or external storage medium, including on a single storage medium or distributed across multiple storage mediums.

Figure 2:
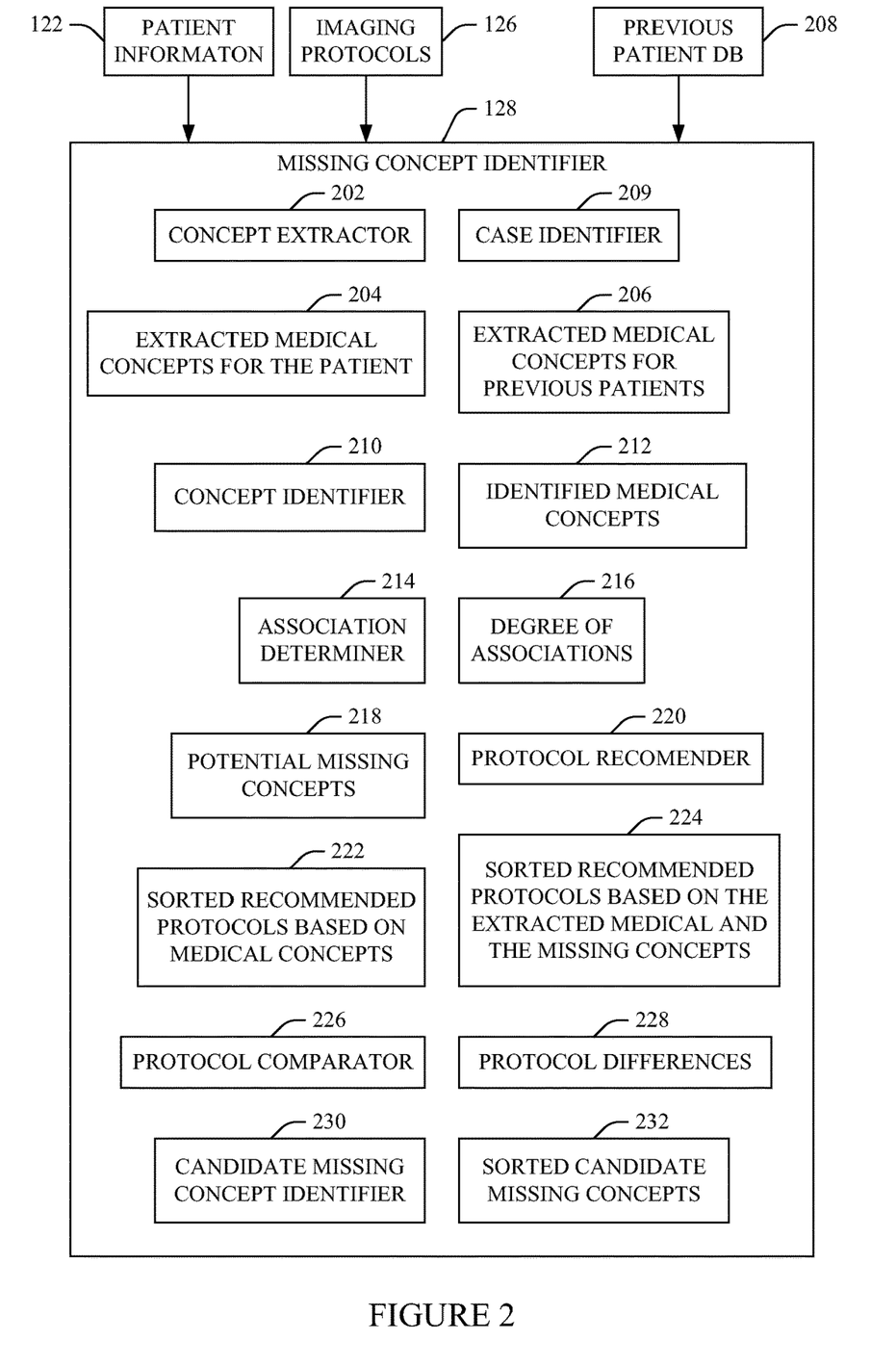
FIG. 2 illustrates an example missing concept identifier.

FIG. 2 illustrates an example of the missing concept identifier 128.

A concept extractor 202 extracts medical concepts (extracted medical concepts for the patient 204) such as clinical indications from the patient information 122. The concept extractor 202 also extracts medical concepts for previously scanned other patients (extracted medical concepts for previous patients 206) from a previously scanned patient information database (previous patient DB 208). Where the information 122 includes free text, the concept extractor 202, optionally, can employ a natural language processing algorithm or the like to extract a list of medical concepts that may be given as strings (e.g. "tinnitus"), coded values (e.g. "UMLS:C0040264"), and/or other text based format.

A case identifier 209 compares the extracted medical concepts for the patient 204 with the extracted medical concepts for the previous patients 206 and identifies cases of previously scanned patients from the DB 208 that include the medical concepts in the extracted medical concepts for the patient 204.

A concept identifier 210 identifies medical concepts 212 in the identified cases that are absent from the extracted medical concepts for the patient 204.

An association determiner 214 determines degree of associations 216, which represents a degree of association between the extracted medical concepts for the patient 204 and one or more of the extracted medical concepts for the previous patients 206. Associations between medical concepts could be obtained from different sources to build a database of known associations. The associations can be specified manually by medical experts or they could be derived from data. In the latter case, the associations could be identified through co-occurrence frequencies between medical concept terms in a collection of reports, or scholarly articles (e.g. medical journals), clinical textbooks on specific domains.

Potential missing concepts 218 are determined based on the degrees of associations 216. A missing concept is identified as a potential missing concept 218 in response to the corresponding degree of association satisfying a predetermined threshold. The potential missing concepts 218 can be sorted based on degree or other sorting criteria. Techniques such as statistical techniques (e.g., Fisher's exact test, Chi-square test, etc.) can be employed to select suitable ones of the identified concepts as the potential missing concepts 218. The remaining concepts can be discarded.

A protocol recommender 220 evaluates the extracted medical concepts for the patient 204 and recommends a set of sorted recommended protocols based on medical concepts 222 for the patient (from the protocols in the imaging protocols 126) based on the evaluation. The protocol recommender 220 also evaluates, in combination, the extracted medical concepts for the patient 204 and different combination of the one or more potential missing concepts 218, and recommends a set of sorted recommended protocols based on extracted medical and potential missing concepts 224 for the patient for each combination (from the protocols in the imaging protocols 126) based on the evaluation. The protocol recommender 220 can employ rules, probabilities, similarity metrics, etc., and, in this example, sorts the protocols based on appropriateness for the patient and/or other sorting criteria. An example of a suitable protocol recommender 220 is described in concurrently filed PCT application PCT/IB12/50446 on Jan. 31, 2012 claiming priority to provisional application 61/439,476 concurrently filed on Feb. 4, 2011 with provisional application 61/439,484 of the present application and entitled "IMAGING PROTOCOL UPDATE AND/OR RECOMMENDER," which is incorporated herein by reference in its entirety.

A protocol comparator 226 compares the list of sorted recommended protocols 222 with each (or a sub-set of) the sorted recommended protocols 224 and determines protocol differences 228, which indicates whether the set of recommended protocol 222 and one or more of the sets of the recommended protocols 224 match or are different (e.g., re-ordered, includes all or some different protocols, a combination thereof, etc.).

A candidate missing concept identifier 230 identifies as candidate missing concepts 232 (which are sorted in the illustrated embodiment) the potential missing concepts 218 that resulted in one or more of the protocol differences 228. Concepts from the potential missing concepts 218 that did not result in any changes in the sorted protocols can be discarded or otherwise deemed as likely not to be relevant missing concepts for protocoling. A list of the identified candidate missing concepts can be sorted based on the degree of difference between the first set of protocols and the corresponding set of protocols.

The missing concept identifier 128 outputs the list 232. In a variation of the above, the protocol recommender 220 is omitted, and the missing concept identifier 128 outputs the potential missing concepts 218.

One or more of the patient information 122, the imaging protocols 126, the extracted medical concepts for the patient 204, the extracted medical concepts for the previous patients 206, the identified medical concepts 212, the degree of associations 216, the potential missing concepts 218, the sorted recommended protocols 222 and/or 224, the list 232, and/or other information can be displayed via the display 119 and/or other display, and/or conveyed to another computing apparatus.

Such information can be variously presented based on a default configuration, user preferences, and/or otherwise. By way of example, in one instance, the sorted candidate list and/or the potential missing concepts 218 is concurrently displayed with the protocols. Where the user is interested in seeing the influence of one (or more) concept, the user selects the concept (e.g. via clicking on the concepts using a mouse or other pointing device), and one or more sorted protocol lists, with and without the selected concept(s), are concurrently displayed. Such information may be visually highlighted and/or otherwise visually emphasized. Statistics may also be presented. Such statistics may indicate the way the candidate relevant additional concept is affecting the sorted list of protocols.

The user of the system 102 can select a candidate missing concept and employ and/or save the resulting protocol for the patient. The protocol can be conveyed from the computing system 102 to another system such as the imaging scanner that will be to scan the patient using proprietary and/or standard approaches such as by encoding the protocol as a RIS Procedure ID and transmitting via the DICOM modality worklist. The protocol can be automatically loaded and loaded via user interaction.

Figure 3:
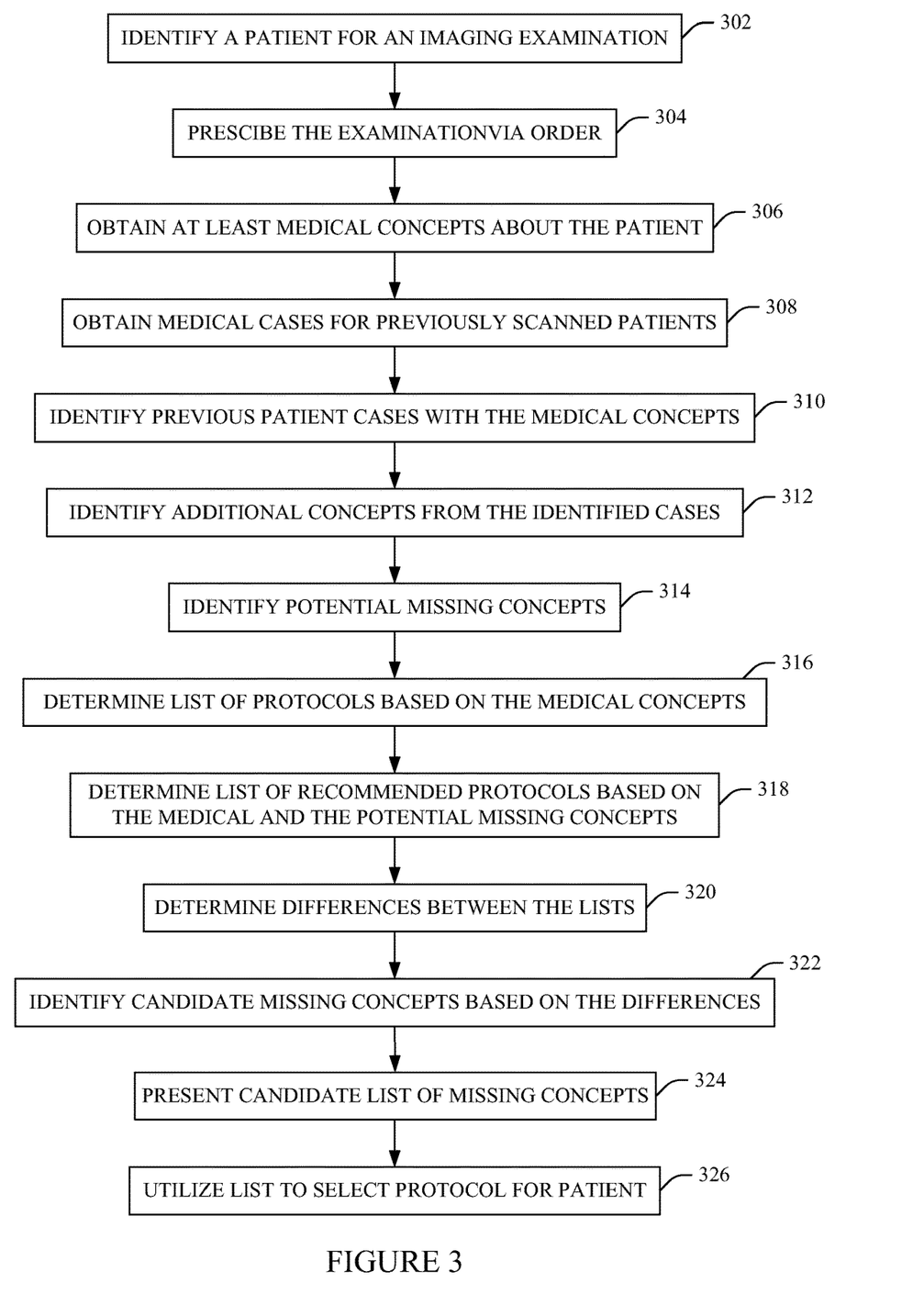
FIG. 3 illustrates an example method for identifying missing concepts for protocoling.

FIG. 3 illustrates an example method for identifying candidate missing medical concepts for protocoling. It is to be appreciated that the ordering of the acts in the methods described herein is not limiting. As such, other orderings are contemplated herein. In addition, one or more acts may be omitted and/or one or more additional acts may be included.

At 302, a patient is identified to be imaged via an imaging system.

At 304, a referring physician prescribes an imaging examination via an order that includes medical concepts such as clinical indications (e.g., signs and symptoms) and/or other information.

At 306, electronically formatted clinical medical information about the patient is obtained. Such information includes at least the medical concepts for the patient to be scanned.

At 308, electronically formatted clinical information, including cases, about previously scanned patients is obtained.

At 310, patient cases from the information about previously scanned patients that include the same medical concepts are identified.

At 312, other medical concepts from the identified patient cases that are absent from the medical concepts for the patient are identified At 314, the other medical concepts determined to be relevant to protocoling based on their association with the medical concepts for the patient to be scanned are identified and used to produce a set of potential missing concepts.

At 316, a sorted list of protocols recommended for the patient based on the extracted medical concepts for the patient is generated. The list is sorted based on a degree of appropriateness of the protocols for the patient based on the based on the medical concepts for the patient.

At 318, one or more other sorted lists of protocols recommended for the patient based on a combination of the medical concepts for the patient to be scanned and one or more combinations of the potential missing concepts is generated. Likewise, the list is sorted based on a degree of appropriateness of the protocols for the patient based on the based on the medical concepts for the patient.

At 320, differences, if any, between the sorted list of protocols (from act 316) and the one or more other sorted lists of protocols (from act 318) are identified.

At 322, the potential missing concepts resulting in the differences are identified as candidate missing concepts for protocoling.

At 324, at least the sorted list of the candidate missing concepts is visually presented via a display. In this example, the list is sorted based on a degree of the difference between the sorted lists of protocols.

At 326, at least the presented list of sorted candidate missing concepts is utilized for selecting a suitable protocol for the patient to be scanned.

The above may be implemented by way of computer readable instructions, which when executed by a computer processor(s), cause the processor(s) to carry out the described acts.

The following provides a non-limiting use-case scenario. The order prescribing the imaging examination includes symptoms A and B. Through one or more of the acts discussed herein, it is determined from information for other patients that symptoms A and B often occur with missing symptoms C, D, or E. A first set of sorted recommended protocols is determined based on symptoms A and B and one or more other sets of sorted recommended protocols is determined based on different combinations of symptoms A and B and one or more of C, D, or E (e.g., A, B and C, A, B and D, A, B, C, and E, etc.). In response to determining that the combination of symptoms A, B and D leads to a different choice in protocol for the patient compared with just using symptoms A and B, the symptom D is then retained and presented for selection as a missing relevant medical concept for selecting a protocol for the patient.

Figure 4:
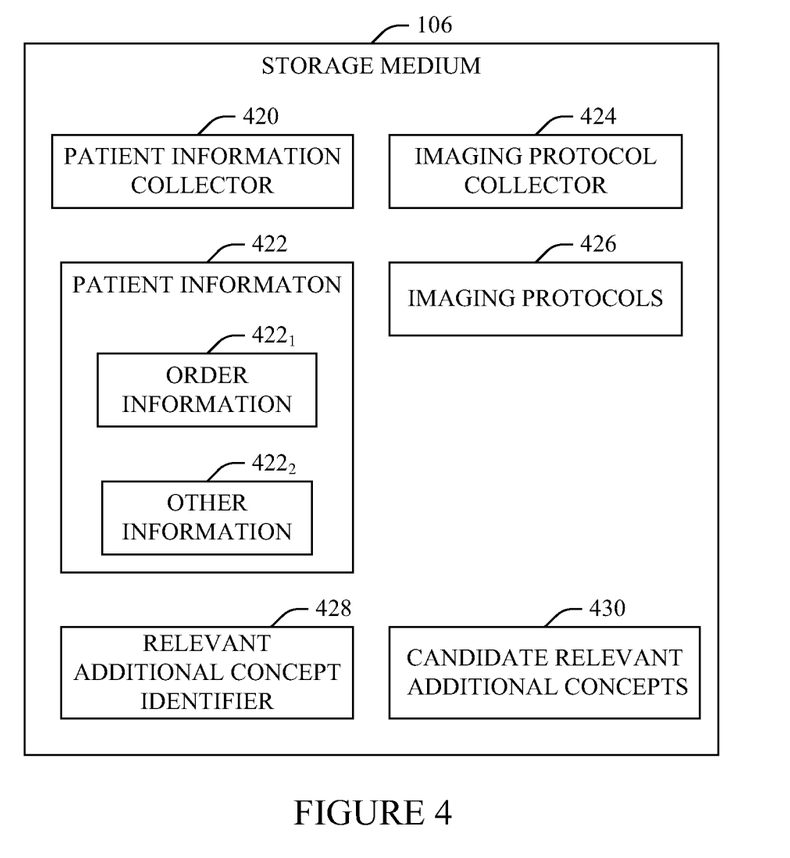
FIG. 4 illustrates an embodiment in which the storage includes computer readable instructions for identifying relevant additional concepts for protocoling.

FIG. 4 illustrates another embodiment in which the storage medium 106 stores various software applications and/or data, which are discussed next. As shown, in the illustrated embodiment, the storage medium 106 includes at least a patient information collector 420, patient information 422, an imaging protocol collector 424, imaging protocols 426, a relevant additional concept identifier 428, and candidate relevant additional concepts 430.

The patient information collector 420 communicates with various data repositories of the one or more data repositories 116 and/or other data repository(s) and retrieves electronically formatted information (the patient information 422) therefrom for a particular subject scheduled to be scanned. With continuing reference to the radiology use case scenario, the patient information 422 includes at least a physician prescribed order $422_1$ (with clinical indications such as signs, symptoms, etc.) and other information $422_2$ such as laboratory information, prior imaging reports, prior non-imaging reports, and/or other information.

The imaging protocol collector 424 also communicates with various data repositories of the one or more data repositories 116 and/or other data repository(s) and retrieves electronically formatted information therefrom. With continuing reference to imaging, the imaging protocol collector 424 at least collects the imaging protocols 426.

The relevant additional concept identifier 428 identifies the candidate relevant additional concepts 430 that are likely to facilitate protocoling and that are present in the patient information 422. As described in greater detail below, in one instance, this is achieved by determining whether and how much a medical concept in the other information $422_2$ impacts a list of recommended protocols determined based on the physician prescribed order $422_1$ without the other information $422_2$, and identifying one or more of the medical concepts as the candidate relevant additional concepts 430 based on the impact.

A candidate relevant additional concept, in response to being confirmed as a relevant additional concept 430, may be displayed and used to facilitate mitigating sub-optimal protocoling due at least in part to protocoling without the candidate relevant additional concept 430. Confirmation can be achieved through input provided by a user of the system 102, and may involve interaction therebetween. The relevant additional concepts may lead to a more refined view of the patient condition and improved protocol selection.

In the illustrated embodiment, the patient information collector 420, the patient information 422, the imaging protocol collector 424, the imaging protocols 426, the relevant additional concept identifier 428, and the candidate relevant additional concepts 430 are shown in the storage medium 106. However, it is to be appreciated that one or more of 420-430 can be located in other local storage medium and/or external storage medium, including on a single storage medium or distributed across multiple storage mediums.

Figure 5:
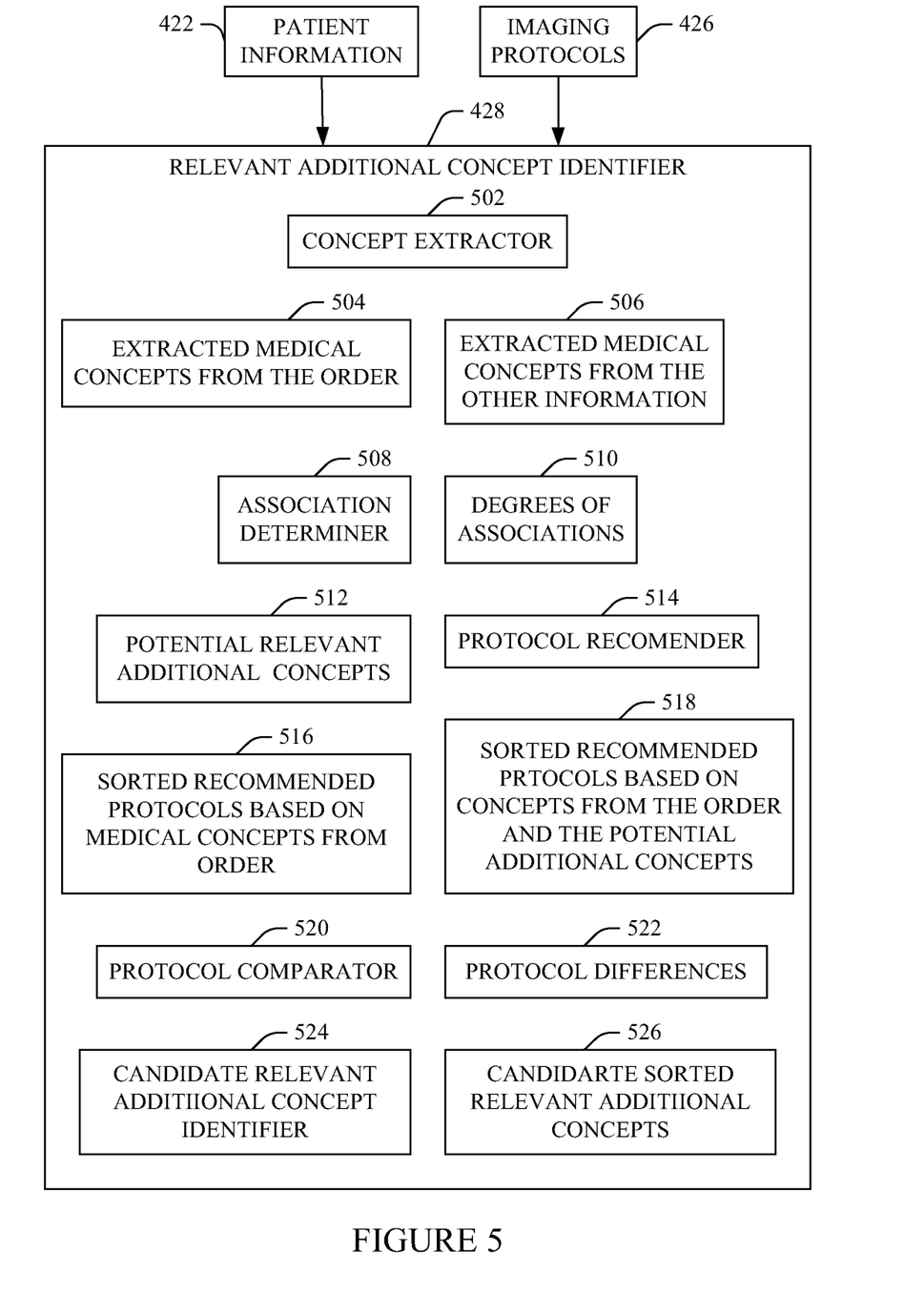
FIG. 5 illustrates an example relevant additional concept identifier.

FIG. 5 illustrates an example of the relevant additional concept identifier 428.

A concept extractor 502 extracts a first set of medical concepts (extracted medical concepts from the order 504) such as clinical indications from the order information $422_1$ (FIG. 4) and extracts a second set of medical concepts (extracted medical concepts from the other information 506) from the other information $422_2$ (FIG. 4). Where the information 422 includes free text, the concept extractor 502, optionally, can employ a natural language processing algorithm or the like to extract a list of medical concepts that may be given as strings (e.g. "tinnitus"), coded values (e.g. "UMLS:C0040264"), and/or other text based format.

An association determiner 508 determines degrees of associations 510, which represents a degree of association between the extracted medical concepts from the order 504 and each of the extracted medical concepts from the other information 506. Associations between medical concepts could be obtained from different sources to build a database of known associations. The associations can be specified manually by medical experts or they could be derived from data. In the latter case, the associations could be identified through co-occurrence frequencies between medical concept terms in a collection of reports, or scholarly articles (e.g. medical journals), clinical textbooks on specific domains.

Potential relevant additional concepts 512 are determined based on the degrees of associations 510. A relevant additional concept is identified as a potential relevant additional concept 512 in response to the corresponding degree of association satisfying a predetermined threshold. The potential relevant additional concepts 512 can be sorted based on degree or other sorting criteria. Techniques such as statistical techniques (e.g., Fisher's exact test, Chi-square test, etc.) can be employed to select suitable ones of the identified concepts as the potential relevant additional concepts 512. The remaining concepts can be discarded.

A protocol recommender 514 evaluates the extracted medical concepts from the order 504 and generates a set of sorted recommended protocols based on medical concepts from order 516 for the patient (from the protocols in the imaging protocols 426) based on the evaluation. The protocol recommender 514 also evaluates, in combination, the extracted medical concepts from the order 504 and different combinations of the one or more potential relevant additional concepts 512, and generates a set of sorted recommended protocols based on the concepts from the order and the potential relevant additional concepts 518 for the patient for each combination (from the protocols in the imaging protocols 426) based on the evaluation. The protocol recommender 520 can employ rules, probabilities, similarity metrics, etc., and, in this example, sorts the protocols based on appropriateness for the patient and/or other sorting criteria. An example of a suitable protocol recommender 514 is described in concurrently filed PCT application PCT/IB12/50446 on Jan. 31, 2012 claiming priority to provisional application 61/439,476 concurrently filed on Feb. 4, 2011 with provisional application 61/439,484 of the present application and entitled "IMAGING PROTOCOL UPDATE AND/OR RECOMMENDER," which, as state above, is incorporated herein by reference in its entirety.

A protocol comparator 520 compares the list of sorted recommended protocols 516 with each (or a sub-set of) the sorted recommended protocols 518 and determines protocol differences 522, which indicates whether the set of recommended protocols 516 and one or more of the sets of the recommended protocols 518 match (e.g., no changer or substantially the same) or are different (e.g., re-ordered, includes all or some different protocols, a combination thereof, etc.) based on a predetermined threshold level.

A candidate relevant additional concept identifier 524 identifies as candidate relevant additional concepts 526 the potential relevant additional concepts 512 that resulted in one or more of the protocol differences 522. Concepts from the relevant additional concepts 512 that did not result in any meaningful change in the sorted protocols can be discarded or otherwise deemed as likely not to be relevant additional concepts for protocoling. A list of the identified candidate relevant additional concepts can be sorted based on the degree of difference between the first set of protocols and the corresponding set of protocols.

The relevant additional concept identifier 428 outputs the list 526. In a variation of the above, the protocol recommender 514 is omitted, and the relevant additional concept identifier 428 outputs the potential relevant additional concepts 512.

One or more of the patient information 422, the imaging protocols 426, the extracted medical concepts from the order 504, the extracted medical concepts from the other information 506, the potential relevant additional concepts 512, the degree of associations 510, the sorted recommended protocols 516 and/or 518, or the list 526, and/or other information can be displayed via the display 119 and/or other display, and/or conveyed to another computing apparatus.

Such information can be variously presented based on a default configuration, user preferences, and/or otherwise. By way of example, in one instance, the sorted candidate list and/or the potential relevant additional concepts 512 is concurrently displayed with the protocols. Where the user is interested in seeing the influence of one (or more) candidate relevant additional concept, the user selects a displayed concept (e.g. via clicking on the concepts using a mouse or other pointing device), and one or more sorted protocol lists, with and without the selected concept(s), are concurrently displayed. Such information may be visually highlighted and/or otherwise visually emphasized. Statistics may also be presented. Such statistics may indicate the way the candidate relevant additional concept is affecting the sorted list of protocols.

The user of the system 102 can select a candidate relevant additional concept and employ and/or save the resulting protocol for the patient. The protocol can be conveyed from the computing system 102 to another system such as the imaging scanner that will be to scan the patient using proprietary and/or standard approaches such as by encoding the protocol as a RIS Procedure ID and transmitting via the DICOM modality worklist. The protocol can be automatically loaded and loaded via user interaction.

Figure 6:
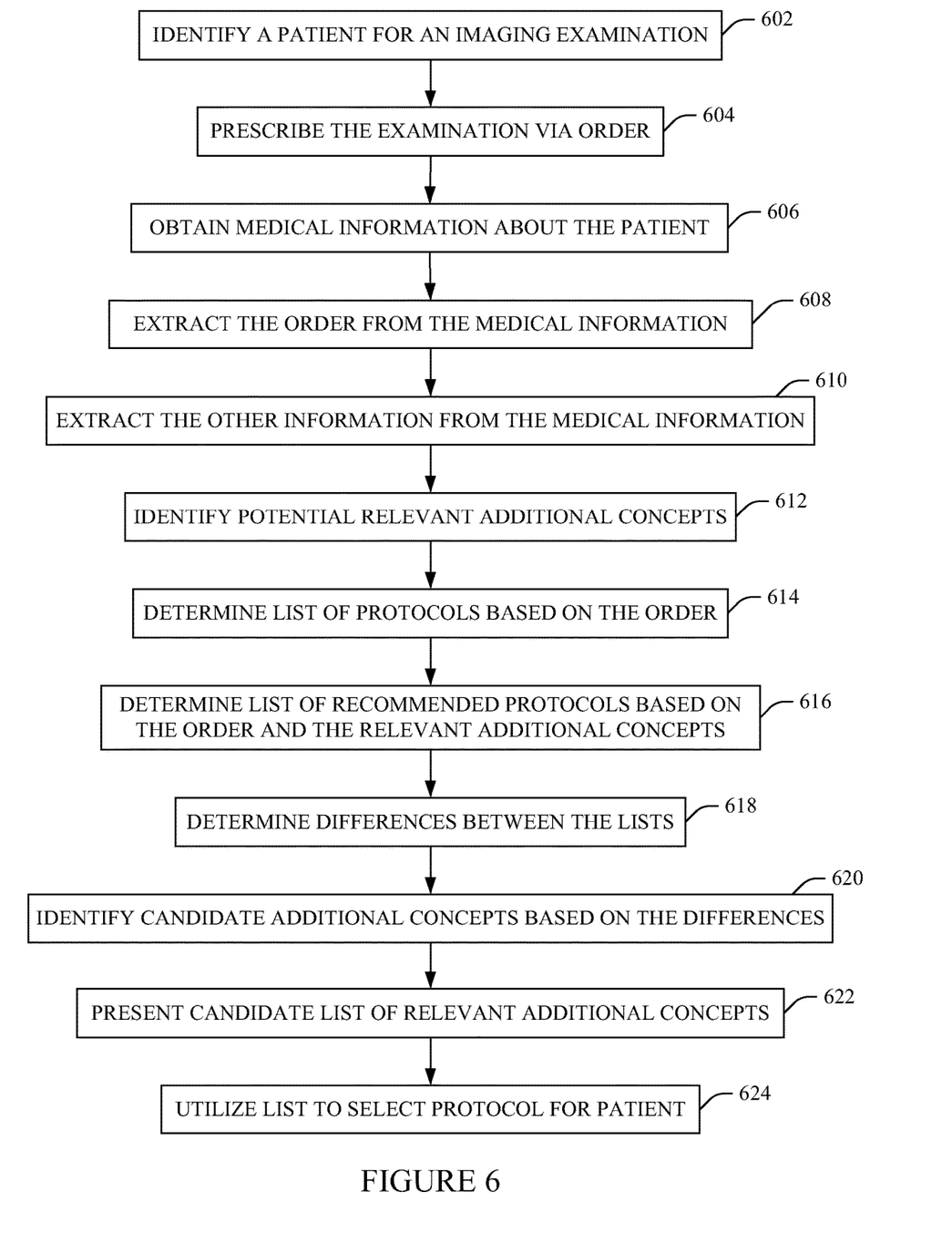
FIG. 6 illustrates an example method for identifying relevant additional concepts for protocoling.

FIG. 6 illustrates an example method for identifying candidate additional medical concepts for protocoling.

It is to be appreciated that the ordering of the acts in the methods described herein is not limiting. As such, other orderings are contemplated herein. In addition, one or more acts may be omitted and/or one or more additional acts may be included.

At 602, a patient is identified to be imaged via an imaging system.

At 604, a referring physician prescribes an imaging examination via an order that includes medical concepts such as clinical indications (e.g., signs and symptoms) and/or other information.

At 606, electronically formatted clinical medical information about the patient is obtained. Such information includes the order (the medical concepts, clinical indications, etc. therein) and/or other information.

At 608, the order is extracted from the clinical medical information.

At 610, other information is extracted from the clinical medical information.

At 612, potential relevant additional concepts from the other information are identified based on their association with the medical concepts in the order.

At 614, a sorted list of protocols recommended for the patient based on the order is generated. The list is sorted based on a degree of appropriateness of the protocols for the patient based on the based on the medical concepts for the patient.

At 616, one or more other sorted lists of protocols recommended for the patient based on a combination of the order and one or more combinations of the potential relevant additional medical concepts is generated. Likewise, the list is sorted based on a degree of appropriateness of the protocols for the patient based on the based on the medical concepts for the patient.

At 618, differences, if any, between the sorted list of protocols (from act 614) and the one or more other sorted lists of protocols (from act 616) are identified.

At 620, the potential relevant additional concepts resulting in the differences are identified as candidate relevant additional concepts for protocoling.

At 622, at least the sorted list of the candidate relevant additional concepts is visually presented via a display. The lists from acts 614 and/or 616 may also be displayed.

At 624, the presented list of sorted candidate relevant additional concepts is utilized for selecting a suitable protocol for the patient to be scanned.

The above may be implemented by way of computer readable instructions, which when executed by a computer processor(s), cause the processor(s) to carry out the described acts.

The following provides a non-limiting use-case scenario. The order prescribing the imaging examination includes symptoms A and B. Through one or more of the acts discussed herein, it is determined that symptoms C, D, E, and other symptoms are found in the other information about this patient. Further, it is found symptoms A and B often occur in other patients with relevant additional symptoms C, D, or E, i.e. that these are potentially relevant symptoms. A first set of sorted recommended protocols is determined based on symptoms A and B and one or more other sets of sorted recommended protocols is determined based on different combinations of symptoms A and B and one or more of C, D, or E (e.g., A, B and C, A, B and D, A, B, C, and E, etc.). In response to determining that the combination of symptoms A, B and D leads to a different choice in protocol for the patient compared with just using the symptoms from the incoming order, A and B, the symptom D is then retained and presented for selection as a additional relevant medical concept for selecting a protocol for the patient.

The invention has been described with reference to preferred embodiments. Modifications and alterations may occur to others upon reading and understanding the preceding detailed description. It is intended that the invention be constructed as including all such modifications and alterations insofar as they come within the scope of the appended claims or the equivalents thereof.

What is claimed is:

1. A method, comprising:
   obtaining first electronically formatted medical information about a patient scheduled for an imaging procedure via an imaging system, wherein the electronically formatted medical information includes a first set of medical concepts corresponding to the imaging procedure;
   obtaining second electronically formatted medical information with a second set of medical concepts for one or more imaging procedures for other patients previously scanned;
   identifying cases of the other patients that correspond to the second electronically formatted medical information wherein the second set of medical concepts comprise the first set of medical concepts;
   identifying a third set of medical concepts in the second set of medical concepts from identified cases of other patients that are missing from the first set of medical concepts in the first electronically formatted medical information of the patient as missing medical concepts; and
   selecting an imaging protocol for the imaging procedure from imaging protocols recommended for the missing medical concepts, and generating a signal indicative of the selected imaging protocol that configures an imaging scanner to scan the patient.

2. The method of claim 1, wherein obtaining second electronically formatted medical information with medical concepts includes:
   obtaining the second electronically formatted medical information from a database of information for previously scanned other patients, wherein the second electronically formatted medical information includes the third set of medical concepts utilized to select imaging protocols for the previously scanned other patients.

3. The method of claim 1, wherein identifying the third set of medical concepts in the identified cases of other patients includes:
   obtaining degrees of association between the first set of medical concepts from the first electronically formatted medical information and each of at least a sub-set of the identified third set of medical concepts from the second electronically formatted medical information that are missing from the first set of medical concepts in the first electronically formatted medical information, wherein the obtained degrees of association are stored in a database of medical concepts and degrees of association;
   comparing each of the obtained degrees of association with a predetermined threshold level; and
   selecting identified medical concepts as missing medical concepts in response to a corresponding degree of association satisfying a predetermined threshold level.

4. The method of claim 3, further comprising:
   discarding at least one identified medical concept of the third set from the second electronically formatted medical information in response to the corresponding degree of association not satisfying the predetermined threshold level.

5. The method of claim 3, further comprising:
   sorting the missing medical concepts based on the obtained degrees of association.

6. The method of claim 3, wherein the degrees of association obtained from the database of medical concepts and degrees of association comprise a measure of co-occurrence frequencies of the first set of medical concepts and the third set of medical concepts in a plurality of documents, wherein the plurality of documents include at least one selected from a group comprised of medical journals and clinical textbooks.

7. The method of claim 1, further comprising:
determining a first list of recommended imaging protocols according to the first set of medical concepts from the first electronically formatted medical information and combinations of the missing medical concepts.

8. The method of claim 7, further comprising:
determining a second list of recommended imaging protocols according to the first set of medical concepts of the first electronically formatted medical information; and
determining a difference in recommended imaging protocols between the first list and the second list, wherein the determined difference in recommended imaging protocols forms the imaging protocols recommended for the missing medical concepts.

9. The method of claim 7, wherein selecting an imaging protocol for the imaging procedure includes selecting from a displayed list of the imaging protocols recommended for the missing medical concepts ordered by missing medical concept.

10. The method of claim 8, further comprising:
displaying the first and second lists; and
visually highlighting the differences between the lists.

11. The method of claim 8, further comprising:
displaying the missing medical concepts in an ordered list.

12. The method of claim 11, further comprising:
receiving an input indicative of at least one displayed missing medical concept of the displayed missing medical concepts; and
determining and displaying a list of recommended protocols based on the received input indicative of at least one displayed missing medical concept.

13. The method of claim 8, further including:
operating the imaging scanner to scan the patient according to the selected imaging protocol.

14. The method of claim 8, wherein the imaging scanner comprises at least one modality selected from a group comprising of computed tomography (CT), magnetic resonance (MR), positron emission tomography (PET), X-ray, ultrasound (US), and nuclear medicine (NM).

15. A computing system, comprising:
computer readable non-transitory storage medium encoded with instructions for determining one or more scan protocols for a patient to be scanned;
one or more processors configured to execute the instructions, wherein the one or more processors, when executing the instructions:
identify at least one medical concept utilized for selecting an imaging protocol for a previously scanned other patient as a missing medical concept in connection with patient information for the patient to be scanned, wherein the identified at least one medical concept is absent from the patient information for the patient to be scanned and one or more medical concepts in the patient information for the patient to be scanned are included in medical concepts for the previously scanned other patient; and
determine at least one scan protocol utilized by an imaging scanner to scan the patient to be scanned which corresponds to the missing medical concept and the one or more medical concepts; and
generate a signal indicative of the determined at least one scan protocol that configures the imaging scanner to scan the patient; and
a display configured to display the missing medical concept and the determined at least one scan protocol.

16. The computing system of claim 15, wherein the one or more processors are further configured to:
receive an input indicative of a selected protocol from the determined at least one scan protocol; and
provide a signal to operate an imaging scanner according the selected protocol.

17. The computing system of claim 16, further comprising:
the imaging scanner configured receive the signal and to scan the patient to be scanned according to the selected protocol.

18. The computing system of claim 16, wherein the imaging scanner comprises at least one modality selected from a group comprising of computed tomography (CT), magnetic resonance (MR), positron emission tomography (PET), X-ray, ultrasound (US), and nuclear medicine (NM).

19. A computer readable storage medium encoded with instructions which when executed by a processor cause the processor to:
obtain first electronically formatted medical information about a patient scheduled for an imaging procedure via an imaging system, wherein the electronically formatted medical information includes a first set of medical concepts corresponding to the imaging procedure;
obtain second electronically formatted medical information with a second set of medical concepts for one or more imaging procedures for other patients previously scanned;
identify cases of the other patients that correspond to the second electronically formatted medical information wherein the second set of medical concepts comprise the first set of medical concepts;
identify a third set of medical concepts in the second set of medical concepts from identified cases of other patients that are missing from the first set of medical concepts in the first electronically formatted medical information of the patient as missing medical concepts; and
select an imaging protocol for the imaging procedure from imaging protocols recommended for the missing medical concepts; and
generate a signal indicative of the selected imaging protocol that configures an imaging scanner to scan the patient.

20. The non-transitory computer readable storage medium of claim 19, wherein the instructions further cause the processor to:
determine a first list of recommended imaging protocols according to the first set of medical concepts from the first electronically formatted medical information and combinations of the missing medical concepts;
determine a second list of recommended imaging protocols according to the first set of medical concepts of the first electronically formatted medical information;
determine a difference in recommended imaging protocols between the first list and the second list, wherein the determined difference in recommended imaging protocols forms the imaging protocols recommended for the missing medical concepts;
display the first and second lists; and
visually highlight the differences between the lists.

* * * * *